(12) United States Patent
Anderson et al.

(10) Patent No.: US 7,547,789 B2
(45) Date of Patent: Jun. 16, 2009

(54) PROCESS FOR THE PREPARATION OF N-(4-PIPERIDINYL)-N-ETHYL-PHENYLACETAMIDES FROM N-BOC-4-OXOPIPERIDINE

(75) Inventors: Emma Anderson, Leicestershire (GB); John Pavey, Leicestershire (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 11/793,284

(22) PCT Filed: Dec. 14, 2005

(86) PCT No.: PCT/GB2005/004815

§ 371 (c)(1),
(2), (4) Date: Jun. 18, 2007

(87) PCT Pub. No.: WO2006/064221

PCT Pub. Date: Jun. 22, 2006

(65) Prior Publication Data

US 2008/0214824 A1    Sep. 4, 2008

(30) Foreign Application Priority Data

Dec. 17, 2004 (SE) .................................... 0403084

(51) Int. Cl.
*C07D 211/58* (2006.01)
(52) U.S. Cl. ..................................................... 546/224
(58) Field of Classification Search .................. 546/224
See application file for complete search history.

(56) References Cited

U.S. PATENT DOCUMENTS

2003/0114517 A1    6/2003    Greenlee et al.

FOREIGN PATENT DOCUMENTS

| WO | WO 00/59497 | 10/2000 |
|----|-------------|---------|
| WO | WO 01/25200 | 4/2001  |
| WO | WO 03/042177 | 5/2003 |
| WO | WO 03/042205 | 5/2003 |
| WO | WO 2005/030209 | 4/2005 |

OTHER PUBLICATIONS

March, J.: "Advanced Organic Chemistry", pp. 818-812m 1977.
Pearson, A.J.: "Handbook of Reagents for Organic Synthesis: Activating Agents and Protecting Groups", pp. 93-96, 1999.
Staab, H. A., et al.: "Azolides in Organic Synthesis and Biochemistry" pp. v-vi and 129-140, 1998.

*Primary Examiner*—Patricia L Morris
(74) *Attorney, Agent, or Firm*—Morgan Lewis & Bockius LLP

(57) ABSTRACT

The present invention concerns a process for the preparation of an N-(4-piperidinyl)-N-ethyl-phenylacetamide of formula (I); wherein $R^1$ and $R^2$ are independently selected from the group comprising: hydrogen, halogen, $C_{1-4}$ alkyl, $C_{1-4}$ alkoxy, cyano and $S(O)_2(C_{1-4}$ alkyl).

1 Claim, No Drawings

PROCESS FOR THE PREPARATION OF N-(4-PIPERIDINYL)-N-ETHYL-PHENYLACETAMIDES FROM N-BOC-4-OXOPIPERIDINE

The present invention concerns a process for preparing N-(4-piperidinyl)-N-ethyl-phenylacetamides which are useful in the preparation of modulators (for example antagonists) of CCR5 chemokine receptor activity.

N-(4-Piperidinyl)-N-ethyl-phenylacetamides are useful pharmaceutical intermediates in the preparation of, for example, N-[1-(3,3-diphenylpropyl)-4-piperidinyl]-N-ethyl-phenyl acetamide derivatives (see for example WO 01/87839). It is known to make N-(4-piperidinyl)-N-ethyl-phenylacetamides via benzyl protected intermediates (see for example WO 01/87839 and WO 03/042177) but not via Boc (tert-butoxycarbonyl) protected intermediates.

The present invention provides a process for the preparation of an N-(4-piperidinyl)-N-ethyl-phenylacetamide of formula (I):

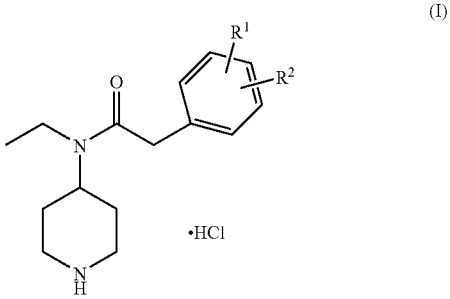

(I)

wherein $R^1$ and $R^2$ are independently selected from the group comprising: hydrogen, halogen, $C_{1-4}$ alkyl, $C_{1-4}$ alkoxy, cyano and $S(O)_2(C_{1-4}$ alkyl); the process comprising the steps of:

a. hydrogenating a mixture of ethylamine and a compound of formula (II) (1-tert-butoxycarbonyl-4-piperidone):

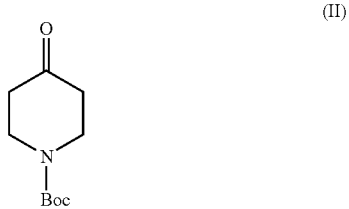

(II)

in a first suitable solvent, in the presence of a suitable catalyst, at a suitable pressure and at a temperature in the range −10 to 160° C. (such as 10 to 80° C.), to form a compound of formula (III) (1-tert-butoxycarbonyl-4-(N-ethylamino)piperidine):

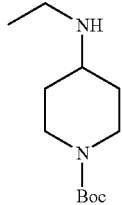

(III)

b. reacting a compound of formula (IV):

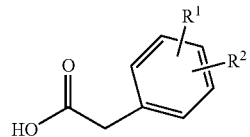

(IV)

with a suitable amine coupling agent, in a suitable solvent (for example an ether or an aromatic solvent) at a temperature in the range −10 to 160° C. (such as 10 to 80° C.); and reacting the product so formed with the compound of formula (III) at a temperature in the range −10 to 160° C. (such as 10 to 80° C.) in a suitable solvent {for example an aromatic solvent, an ether (such as tetrahydrofuran or methyl tert-butyl ether) or an ester (such as ethyl acetate) or a mixture of two or more such solvents}, to form a compound of formula (V):

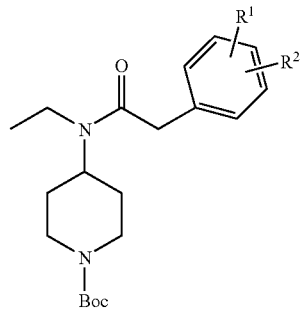

(V)

and, c. forming a compound of formula (I) by treating a compound of formula (V) with HCl in a suitable solvent (such as a second $C_{1-6}$ aliphatic alcohol), at a temperature in the range −10 to 160° C. (such as 10 to 80° C.).

Moving from the known benzyl protected route to the Boc protected process of the present invention there is an unexpected increase in yield from about 64% to over 90%. This yield increase means that there is more efficient use of materials in the process of the invention and the process of the invention has a lower environmental impact than the previously known route. All these factors have a cumulative effect and more than compensate for the higher initial cost of the compound of formula (II) when compared to the corresponding benzyl protected compound. A further advantage of the process of the present invention is that the desired hydrochloride salt (I) is formed directly from the deprotection of (V).

Halogen is, for example, fluoro or chloro.

Alkyl is straight or branched chain and is, for example, methyl, ethyl or iso-propyl.

Alkoxy is straight or branched chain and is, for example, methoxy or ethoxy.

The group $S(O)_2(C_{1-4}$ alkyl) is, for example, $S(O)_2CH_3$.

The formation of a compound of formula (V) can also be achieved by reacting a compound of formula (III) with:

an acid chloride of a compound of formula (IV) (formed, for example, by reacting a compound of formula (IV) with $SOCl_2$, $SO_2Cl_2$, $PCl_5$ or $COCl_2$) in the presence of a base;

an acid anhydride (such as a mixed anhydride) of a compound of formula (IV) in the presence of a base;

the product formed by reacting a $C_{1-6}$ alkyl chloroformate (such as iso-butyl chloroformate) with a compound of formula (IV);

a compound of formula (IV) in the presence of a suitable di-imide reagent {such as DCC (1,3-dicyclohexylcarbodiimide) or EDC (1-(3-dimethylaminopropyl)-3-ethyl-carbodiimide)};

a compound of formula (IV) in the presence of a suitable coupling agent {such as BOP (benzotriazol-1-yloxy-tris(dimethylamino)phosphonium hexafluoro-phosphate), HATU (O-(7-azabenzotriazol-1-yl)-N,N,N',N'-tetramethyluronium hexafluoro-phosphate), TBTU (2-(1H-benzotriazole-1-yl)-1,1,3,3-tetramethyluronium tetrafluoroborate) or PyBOP (1H-benzotriazole-1-yl-oxy-tris-pyrrolidinophosphonium hexafluorophosphate)}; or, a compound of formula (IV) in the presence of a suitable enzyme or dehydration catalyst (such as $B(OH)_3$).

The ethylamine of step a is, for example, a solution in water or tetrahydrofuran.

The source of hydrogen for the hydrogenation is, for example, from a cylinder of hydrogen. The source of hydrogen can also be from a transfer hydrogenation catalyst (such as formic acid or ammonium formate).

The first suitable solvent can be a single solvent or a mixture of two or more solvents. For example the first suitable solvent comprises a first $C_{1-6}$ aliphatic alcohol (for example in a mixture with an aromatic solvent, such as toluene), an ether (such as tetrahydrofuran) or an ester (such as ethyl acetate). A first aliphatic alcohol is, for example, ethanol or iso-propanol.

A first $C_{1-6}$ aliphatic alcohol is straight or branched chain and is, for example, ethanol.

Suitable catalysts are, for example, Raney-Nickel, or a rhodium, iridium, palladium or platinum catalyst; such as for example palladium or platinum; for example palladium or platinum supported on carbon. Suitable catalysts comprise, for example, 1-15 weight % (especially 4-12%) metal and include 5% palladium on carbon (such as Johnson Matthey types 437, 440, 331, 38H, 39, 398, 472, 58 and 87L; or Engelhard type 5214), 10% palladium on carbon (such as Johnson Matthey type 87L), 5% platinum on carbon (such as Johnson Matthey type 117) or a mixture of palladium and platinum on carbon for example 2.5% palladium, 2.5% platinum on carbon (such as Johnson-Matthey catalyst 5R/121). Typically, these catalysts are about 60% water. A catalyst loading of between 0.1 wt % and 10 wt % of water wet catalyst (with respect to 4-hydroxypiperidine) is preferred.

A suitable pressure is, for example, a pressure of between 1 and 5 bar (such as between 1 and 3 bar, for example about 2 bar).

A suitable amine coupling agent is, for example, carbonyldiimidazole.

A suitable ether solvent is, for example, tetrahydrofuran or methyl tert-butyl ether.

A suitable aromatic solvent is, for example, toluene or xylenes.

A second $C_{1-6}$ aliphatic alcohol is straight or branched chain and is, for example, ethanol or iso-propanol.

In one aspect of the invention $R^1$ is a para-substituent for example para-$S(O)_2(C_{1-4}$ alkyl), such as para-$S(O)_2CH_3$.

In a further aspect of the invention $R^2$ is hydrogen.

The present invention provides a process for the preparation of an N-(4-piperidinyl)-N-ethyl-phenylacetamide of formula (I):

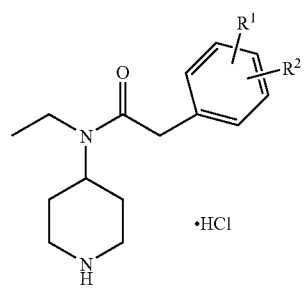

(I)

wherein $R^1$ is $S(O)_2(C_{1-4}$ alkyl), and $R^2$ is hydrogen, halogen, $C_{1-4}$ alkyl, $C_{1-4}$ alkoxy, cyano or $S(O)_2(C_{1-4}$ alkyl) (for example $R^2$ is hydrogen); the process comprising the steps of:

a. hydrogenating a mixture of ethylamine and a compound of formula (II) (1-tert-butoxycarbonyl-4-piperidone):

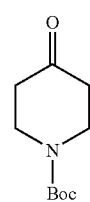

(II)

in a solvent comprising ethanol, in the presence of a suitable palladium or platinum catalyst, at a pressure in the range 1-5 bar and at a temperature in the range 10-80° C., to form a compound of formula (III) (1-tert-butoxycarbonyl-4-(N-ethylamino)piperidine):

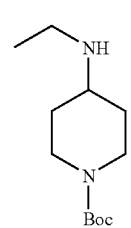

(III)

b. reacting a compound of formula (IV):

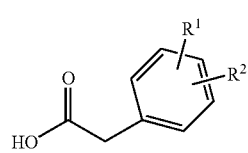

(IV)

with carbonyldiimidazole in an ether or an aromatic solvent, at a temperature in the range 10-80° C.; and reacting the product so formed with the compound of formula (III) at a temperature in the range 10-80° C. in a suitable solvent {for example an aromatic solvent, an ether (such as tetrahydrofuran or methyl tert-butyl ether) or an ester (such as ethyl acetate) or a mixture of two or more such solvents}, to form a compound of formula (V):

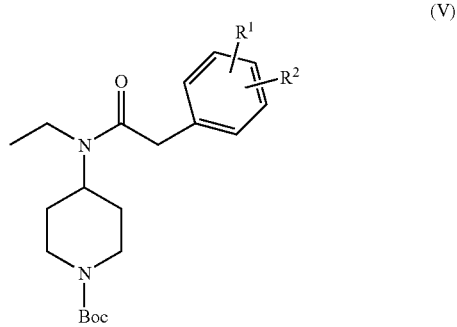

and, c. forming a compound of formula (I) by treating a compound of formula (V) with HCl in a suitable solvent (such as a second $C_{1-6}$ aliphatic alcohol), at a temperature in the range 10-80° C.

The invention will now be illustrated by the following non-limiting Example. In the Example the following apply, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$) or $CDCl_3$ as the solvent unless otherwise stated;

(ii) mass spectra (MS) were run with an electron energy of 70 electron volts in the chemical ionisation (CI) mode using a direct exposure probe; where values for m/z are given, generally only ions which indicate the parent mass are reported, and unless otherwise stated the mass ion quoted is the positive mass ion—$(M+H)^+$; and, (iii) the following abbreviations are used:

| THF | tetrahydrofuran |
| HPLC | high performance liquid chromatography |

EXAMPLE 1

This Example illustrates the preparation of N-(4-piperidinyl)-N-ethyl-4-methanesulfonylphenylacetamide hydrochloride Step 1:

1-tert-Butoxycarbonyl-4-piperidone (15 g, 75.28 mmol) was dissolved in ethanol (150 ml) and treated with 70% ethylamine/$H_2O$ (6.06 ml, 75.29 mmol), followed by 5% Pt/C JM type 117 (2.25 g, 20 wt %). The reaction mixture was subjected to hydrogenation at 2 bar, 50° C. with stiring for 4 hours. The reaction mixture was purged with nitrogen and filtered through GF/F filter paper. The catalyst was washed with ethanol (2×15 ml). The liquors were combined and evaporated to dryness to give N-(1-tert-butoxycarbonyl-4-piperidinyl)ethylamine as a colourless oil (18.33 g, 107%).

$^1$H NMR (400 MHz, $CDCl_3$): δ 4.04 (s, 2H), 2.78 (t, 2H), 2.68 (q, 2H), 2.64-2.58 (m, 1H), 1.84 (d, 2H), 1.48 (s, 9H), 1.29-1.19 (m, 2H), 1.11 (t, 3H).

Step 2:

A slurry of carbonyldiimidazole (1.94 g, 11.98 mmol) in THF (10 ml) was treated with a solution of 4-methylsulphonylphenylacetic acid (2.5 g, 11.68 mmol) in THF (12.5 ml) at ambient temperature and then heated to 50° C. After one hour carbonyldiimidazole (0.189 g, 1.17 mmol) was added. After a further 15 minutes a solution of N-(1-tert-butoxycarbonyl-4-piperidinyl)ethylamine (2.53 g, 11.10 mmol) in toluene (10 ml) was added dropwise over two minutes to the reaction mixture. After 30 minutes at 50° C. the reaction mixture was treated with 1M NaOH (12.5 ml) and the mixture was stired rapidly for 30 min and then allowed to cool to room temperature. The organic layer was separated and washed with aqueous citric acid (10% w/w, 10 ml) and then with water (5 ml). The organic layer was evaporated to dryness to afford N-(1-tert-butoxycarbonyl-4-piperidinyl)-N-ethyl-4-methanesulfonylphenyl-acetamide as a colourless oil (4.75 g, 100%).

$^1$H NMR (300 MHz, $CDCl_3$): δ 7.90 (d, 2H), 7.47 (d, 2H), 4.56-4.43 (m, 0.7H), 4.28-4.11 (m, 2H), 3.83 (s, 0.6H), 3.79 (s, 1.4H), 3.74-3.60 (m, 0.3H), 3.30 (q, 2H), 3.04 (s, 3H), 2.84-2.55 (m, 2H), 1.75-1.53 (m, 4H); 1.46 (s, 9H), 1.25 (t, 2.1H), 1.14 (t, 0.9H).

On a repeat of this method the oil solidified on standing (m.pt. 138-140° C.).

Step 3:

N-(1-tert-Butoxycarbonyl-4-piperidinyl)-N-ethyl-4-methanesulfonylphenyl-acetamide (4.75 g, 11.10 mmol) was slurried in toluene (10 ml) and treated with 5-6M HCl in IPA (10 ml). The mixture was heated to 50° C. for 45 minutes and then cooled to 10° C. in an ice/water bath. The product was collected by filtration, washed with IPA (2×5 ml) and then dried to constant mass in a vacuum oven at 40-45° C. to afford the title compound as a white solid (3.63 g, 90%; melting point 219.5-220.9° C.).

$^1$H NMR (300 MHz, DMSO): δ 7.86 (d, 2H), 7.51 (t, 2H), 4.26 (t, 0.5H), 4.11 (t, 0.5H), 3.92 (s, 1H), 3.84 (s, 1H), 3.41-3.11 (m, 7H), 3.06-2.80 (m, 2H), 2.14-1.95 (m, 2H), 1.69 (t, 2H), 1.16 (t, 1.5H), 1.03 (t, 1.5H).

The invention claimed is:

1. A process for the preparation of an N-(4-piperidinyl)-N-ethyl-phenylacetamide of formula (I):

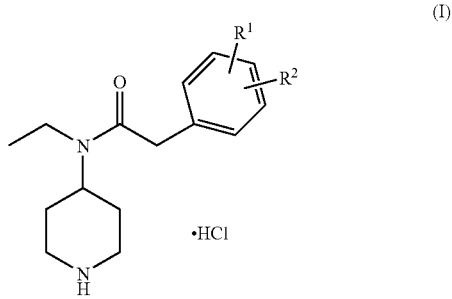

wherein $R^1$ is $S(O)_2(C_{1-4}$ alkyl), and $R^2$ is hydrogen, halogen, $C_{1-4}$ alkyl, $C_{1-4}$ alkoxy, cyano or $S(O)_2(C_{1-4}$ alkyl); the process comprising the steps of:

a. hydrogenating a mixture of ethylamine and a compound of formula (II) (1-tert-butoxycarbonyl-4-piperidone):

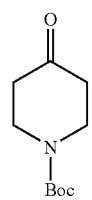

in a solvent comprising ethanol, in the presence of a suitable palladium or platinum catalyst, at a pressure in the range 1-5 bar and at a temperature in the range 10-80° C., to form a compound of formula (III) (1-tert-butoxycarbonyl-4-(N-ethylamino)piperidine):

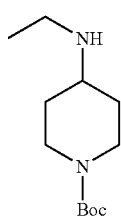

b. reacting a compound of formula (IV):

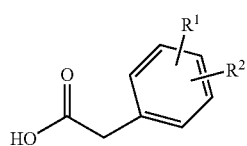

with carbonyldiimidazole in an ether or an aromatic solvent, at a temperature in the range 10-80° C.; and reacting the product so formed with the compound of formula (III) at a temperature in the range 10-80° C. in a suitable solvent, to form a compound of formula (V):

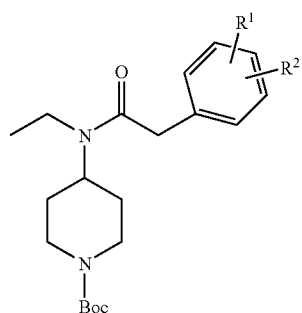

and, c. forming a compound of formula (I) by treating a compound of formula (V) with HCl in a suitable solvent, at a temperature in the range 10-80° C.

* * * * *